(12) United States Patent
Zelenka et al.

(10) Patent No.: US 11,627,869 B2
(45) Date of Patent: *Apr. 18, 2023

(54) IMAGING PROBE HOUSING WITH FLUID FLUSHING

(71) Applicant: ACIST Medical Systems, Inc., Eden Prairie, MN (US)

(72) Inventors: Robert Zelenka, Milpitas, CA (US); Tom Moore, Livermore, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 646 days.

This patent is subject to a terminal disclaimer.

(21) Appl. No.: 16/534,178

(22) Filed: Aug. 7, 2019

(65) Prior Publication Data
US 2019/0357756 A1    Nov. 28, 2019

Related U.S. Application Data

(63) Continuation of application No. 14/795,976, filed on Jul. 10, 2015, now Pat. No. 10,420,456, which is a
(Continued)

(51) Int. Cl.
*A61B 1/015* (2006.01)
*A61B 8/00* (2006.01)
(Continued)

(52) U.S. Cl.
CPC .............. *A61B 1/015* (2013.01); *A61B 1/126* (2013.01); *A61B 1/3137* (2013.01); *A61B 8/0891* (2013.01); *A61B 8/12* (2013.01); *A61B 8/4281* (2013.01); *A61B 8/445* (2013.01); *A61B 8/4461* (2013.01); *A61B 8/4494* (2013.01)

(58) Field of Classification Search
CPC ....... A61B 1/015; A61B 1/126; A61B 1/3137; A61B 8/0891; A61B 8/12; A61B 8/4281; A61B 8/445; A61B 8/4461; A61B 8/4494
See application file for complete search history.

(56) References Cited

U.S. PATENT DOCUMENTS 4,636,346 A    1/1987    Gold et al.
4,870,887 A   10/1989    Tresslar et al.
(Continued)

FOREIGN PATENT DOCUMENTS

CN    1810213 A    8/2006
EP    1955724 A1   8/2008
(Continued)

OTHER PUBLICATIONS

European Patent Application No. 08866090.7, European Supplemental Search Report dated Feb. 5, 2015, 6 pages.
(Continued)

*Primary Examiner* — Peter Luong
(74) *Attorney, Agent, or Firm* — Fredrikson & Byron, P.A.

(57) ABSTRACT

An imaging probe for use in a catheter for ultrasonic imaging is provided. The imaging probe includes a transducer backing and a transducer configured to generate and receive ultrasonic waves. The transducer includes a first surface and a second surface that is opposite the first surface. The first surface faces the transducer backing and the second surface is disposed at an angle sloping toward a catheter center axis in a proximal direction.

20 Claims, 2 Drawing Sheets

Related U.S. Application Data continuation of application No. 13/458,935, filed on Apr. 27, 2012, now Pat. No. 9,198,638, which is a continuation of application No. 12/330,308, filed on Dec. 8, 2008, now Pat. No. 8,167,809.

(60) Provisional application No. 61/008,725, filed on Dec. 20, 2007.

(51) Int. Cl.
*A61B 8/12* (2006.01)
*A61B 1/12* (2006.01)
*A61B 8/08* (2006.01)
*A61B 1/313* (2006.01)

(56) References Cited

U.S. PATENT DOCUMENTS

| | | |
|---|---|---|
| 5,037,404 A | 8/1991 | Gold et al. |
| 5,201,316 A | 4/1993 | Pomeranz et al. |
| 5,240,985 A | 8/1993 | Gardiner |
| 5,250,069 A | 10/1993 | Nobuyoshi et al. |
| 5,312,356 A | 5/1994 | Engelson et al. |
| 5,316,706 A | 5/1994 | Muni et al. |
| 5,330,444 A | 7/1994 | Webler et al. |
| 5,378,100 A | 1/1995 | Fullterton |
| 5,399,164 A | 3/1995 | Snoke et al. |
| 5,400,785 A | 3/1995 | Crowley |
| 5,443,457 A | 8/1995 | Ginn et al. |
| 5,531,721 A | 7/1996 | Pepin et al. |
| 5,542,924 A | 8/1996 | Snoke et al. |
| 5,584,821 A | 12/1996 | Hobbs et al. |
| 5,624,397 A | 4/1997 | Snoke et al. |
| 5,715,825 A | 2/1998 | Crowley |
| 5,720,300 A | 2/1998 | Fagan et al. |
| 5,762,066 A | 6/1998 | Law et al. |
| 5,824,030 A | 10/1998 | Yang et al. |
| 5,851,203 A | 12/1998 | Van Muiden |
| 5,957,910 A | 9/1999 | Holden et al. |
| 6,007,478 A | 12/1999 | Siess et al. |
| 6,159,228 A | 12/2000 | Frid et al. |
| 6,264,633 B1 | 7/2001 | Knorig |
| 6,524,303 B1 | 2/2003 | Garibaldi |
| 6,610,068 B1 | 8/2003 | Yang |
| 6,712,766 B2 | 3/2004 | Harada |
| 6,929,635 B2 | 8/2005 | Shelso |
| 7,387,826 B2 | 6/2008 | Burgmeier et al. |
| 7,632,236 B2 | 12/2009 | Kaneto et al. |
| 2002/0022825 A1 | 2/2002 | Saitou et al. |
| 2002/0188189 A1 | 12/2002 | Belef et al. |
| 2003/0141002 A1 | 7/2003 | Flanagan |
| 2004/0073158 A1 | 4/2004 | Shah |
| 2005/0090852 A1 | 4/2005 | Layne et al. |
| 2005/0101859 A1 | 5/2005 | Maschke |
| 2005/0125002 A1 | 6/2005 | Baran et al. |
| 2005/0142314 A1 | 6/2005 | Burgmeier et al. |
| 2005/0203396 A1 | 9/2005 | Angelsen et al. |
| 2005/0261586 A1 | 11/2005 | Makin et al. |
| 2006/0084964 A1 | 4/2006 | Knudson et al. |
| 2007/0134305 A1 | 6/2007 | Ziberman |
| 2007/0167824 A1 | 7/2007 | Lee et al. |
| 2007/0240817 A1 | 10/2007 | Strong et al. |
| 2009/0163818 A1 | 6/2009 | Zelenka et al. |
| 2009/0270737 A1 | 10/2009 | Thornton |
| 2009/0297582 A1 | 12/2009 | Meyer |
| 2010/0063477 A1 | 3/2010 | Ohigawa |
| 2010/0185172 A1 | 7/2010 | Fabro |
| 2010/0204605 A1 | 8/2010 | Blakley et al. |
| 2011/0091515 A1 | 4/2011 | Ziberman et al. |
| 2012/0252709 A1 | 10/2012 | Felts et al. |
| 2012/0277772 A1 | 11/2012 | Aben et al. |
| 2012/0289837 A1 | 11/2012 | Zelenka et al. |
| 2013/0253328 A1 | 9/2013 | Zelenka et al. |
| 2014/0187964 A1 | 7/2014 | Corl et al. |
| 2014/0276756 A1 | 9/2014 | Hill |
| 2016/0022244 A1 | 1/2016 | Courtney et al. |
| 2017/0071710 A1 | 3/2017 | Deturmeny |

FOREIGN PATENT DOCUMENTS

| | | |
|---|---|---|
| JP | 05084247 A | 4/1993 |
| JP | 08140976 A | 6/1996 |
| JP | 08275947 A | 10/1996 |
| JP | 2000152940 A | 6/2000 |
| JP | 2002109217 A | 4/2002 |
| JP | 2002528188 A | 9/2002 |
| JP | 2003210462 A | 7/2003 |
| JP | 3571939 B2 | 9/2004 |
| JP | 2005006776 A | 1/2005 |
| JP | 2005013453 A | 1/2005 |
| JP | 2005052667 A | 3/2005 |
| JP | 2006075611 A | 3/2006 |
| JP | 2007152101 A | 6/2007 |
| WO | 9221965 A1 | 12/1992 |
| WO | 9850098 A1 | 11/1998 |
| WO | 0033742 A1 | 6/2000 |
| WO | 2009134171 A1 | 11/2009 |
| WO | 2011027821 A1 | 3/2011 |
| WO | 2013169269 A1 | 11/2013 |

OTHER PUBLICATIONS

Giants, "Crystallinity and Dielectric Properties of PEEK, Poly (ether ether ketone)," Abstract, IEEE Transactions on Dielectrics and Electrical Insulation, vol. 1, No. 6, 1994.
International Patent Application No. PCT/US2008/087209, International Search Report dated Aug. 3, 2009, 3 pages.
Japanese Patent Application No. 2010-539741, Office Action dated Jun. 18, 2013, 6 pages (including translation).
Japanese Patent Application No. 2013-225486, Office Action dated Jul. 29, 2014, 4 pages (including translation).
Kurtz et al., "PEEK Biomaterials in Trauma, Orthopedic, and Spinal Implants," Biomaterials, vol. 28, No. 32, 2007, pp. 4845-4869.
U.S. Appl. No. 61/484,941, entitled "Variable-Stiffness Imaging Window and Production Method Thereof," filed May 11, 2011, 19 pages.
English Abstract and Machine Translation for Japanese Publication No. 2005-006776 A, published Jan. 13, 2005, 9 pgs.

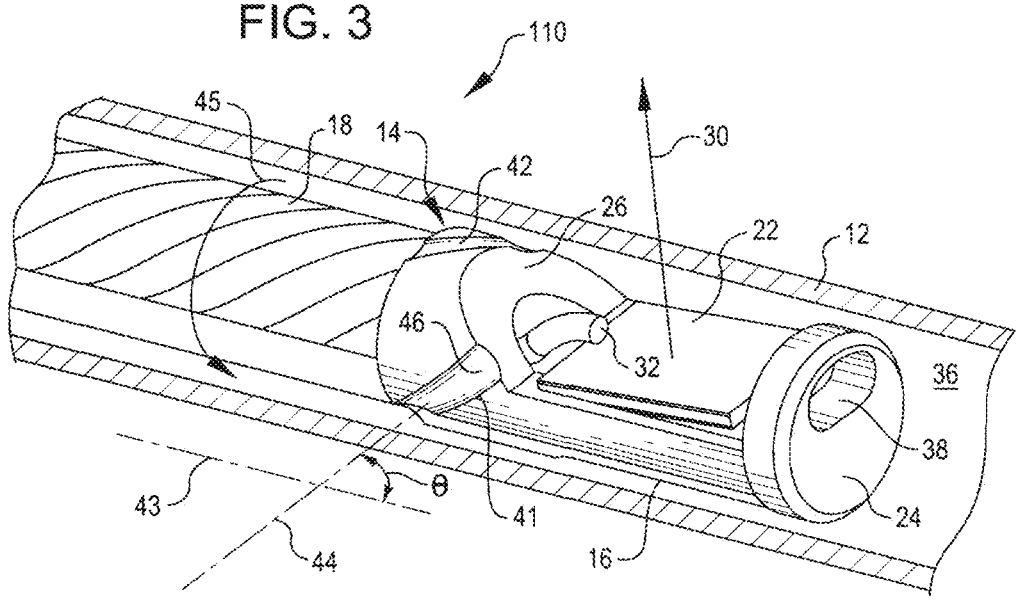

IMAGING PROBE HOUSING WITH FLUID FLUSHING

PRIORITY CLAIM

This application is a continuation of U.S. patent application Ser. No. 14/795,976, filed Jul. 10, 2015, which is a continuation of U.S. patent application Ser. No. 13/458,935, now U.S. Pat. No. 9,198,638, filed Apr. 27, 2012, which is a continuation of U.S. patent application Ser. No. 12/330,308, now U.S. Pat. No. 8,167,809, filed Dec. 8, 2008, which claims the benefit of U.S. Provisional Patent Application No. 61/008,725, filed Dec. 20, 2007. Each of these applications is herein incorporated by reference in their entirety.

BACKGROUND

The present invention generally relates to an imaging probe of an imaging catheter. The present invention more specifically relates to an imaging probe for use in, for example, an intravascular ultrasound (IVUS) catheter. The present invention still further relates to such an imaging probe wherein the imaging probe is configured to assure efficient and complete fluid flushing from the catheter sheath to preclude formation of air bubbles in the vicinity of the ultrasonic transducer of the imaging probe. In addition this invention relates to imaging probe configuration to ensure the prevention of air bubbles during rotational operation by continuously directing fluid across the imaging probes transmission surface.

IVUS catheters enable the imaging of internal structures in the body. Coronary IVUS catheters are used in the small arteries of the heart to visualize coronary artery disease, for example. To that end, an IVUS catheter will employ at least one ultrasonic transducer that creates pressure waves to enable visualization. At least one transducer is usually housed within a surrounding sheath or catheter member and rotated to enable 360 degree visualization. Because air is not an efficient medium for the transmission of the ultrasonic waves produced by at least one transducer, a fluid interface between the transducer and the sheath in which it is disposed is usually provided. Unfortunately, current imaging probe configurations do not always prevent the formation of air bubbles in the fluid in the vicinity of the transducer resulting in compromised performance of the imagining catheter. The present invention addresses this and other issues.

SUMMARY

The invention provides an imaging probe for use in a catheter for ultrasonic imaging. The catheter may include a sheath having an opening at a distal end for conducting a fluid there through. The imaging probe comprises a distal housing coupled to a drive shaft for rotation, a transducer within the distal housing for generating and sensing ultrasonic waves, and a fluid flow promoter that promotes flow of the fluid within the sheath across the transducer.

The imaging probe may further include a wall distal to the transducer and the fluid flow promoter may include an opening within the wall and adjacent to the transducer. The distal housing preferably has a first profile at a proximal end of the distal housing, a second profile at the wall distal to the transducer, and the fluid flow promoter includes the second profile being greater than the first profile to promote fluid flow over the transducer and through the opening within the wall.

The catheter has a center axis and the fluid flow promoter may further include a mounting for the transducer that disposes the transducer at an angle sloping toward the catheter center axis in a proximal direction.

The distal housing has a proximal extent and the fluid flow promoter may include at least one aqua duct within the proximal extent of the distal housing. The at least one aqua duct is preferably formed within the proximal extent of the distal housing at an angle to the center axis. The at least one aqua duct may comprise at least two aqua ducts. The transducer includes a face surface. The at least two aqua ducts may include a first aqua duct that directs fluid directly onto the face surface of the transducer and a second aqua duct that directs fluid onto the face surface of the transducer from a side of the transducer. The at least one aqua duct has a proximal side and a distal side and may be formed so that the proximal side leads the distal side in the direction of rotation of the distal housing. The at least one aqua duct may include a radius of curvature.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 3 is a perspective view showing another imaging probe embodying the invention connected to a drive cable of an intravascular ultrasound (IVUS) catheter.

DETAILED DESCRIPTION

Figure 1:
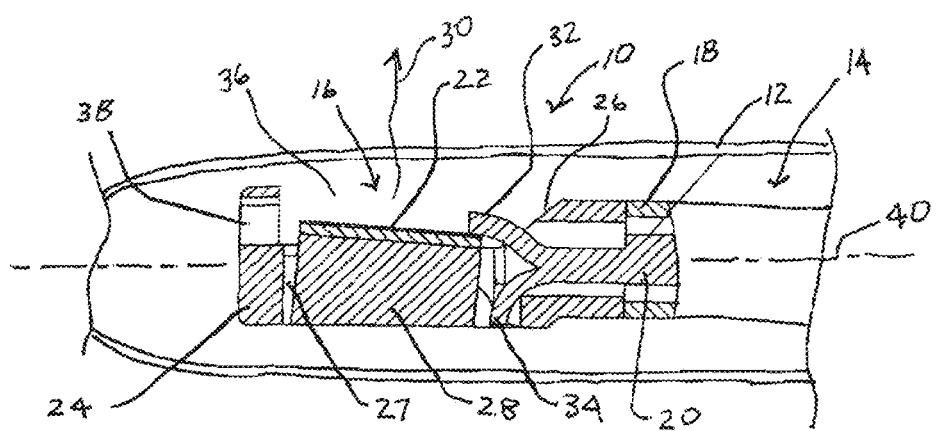
FIG. 1 is a side view, partly in section, of an ultrasonic imaging catheter in accordance with a first embodiment of the invention.

FIG. 1 shows an imaging catheter 10 with the first embodiment of the present invention. The imaging catheter 10 is particularly adapted for use as an IVUS catheter, but those skilled in the art will appreciate that the invention may be used in many other forms of ultrasound catheters as well without departing from the present invention. The catheter 10 generally includes a sheath or catheter member 12 and an imaging probe 14. As shown, the imaging probe 14 is disposed within the sheath 14. The imaging probe 14 is moveable axially within the sheath 12 to enable the sheath to remain stationary as the imaging probe is moved to scan the internal body structures to be visualized. Also, as well known, the imaging probe 14 is also rotatable to enable 360 degree scanning.

The imaging probe 14 generally includes a distal housing 16, a flexible drive shaft 18, and a coaxial cable 20. The distal housing 16 is carried on the distal end of the flexible drive shaft 18 in a known manner. The drive shaft 18 may be formed, for example, by winding multiple strands of metal wire on a mandrel to create a long spring containing a repeating series of concentric rings, or windings, of the wire. Two or more springs may be wound, one over the other, with adjacent springs being wound in opposite directions to each other. This provides a drive shaft that is both flexible and with high torsional stiffness.

The distal housing 16 generally includes the ultrasound transducer 22, a distal tip wall 24, and a proximal cutout surface 26. The transducer 22 is mounted on a transducer backing 28. The backing 28 and the distal tip wall 24 are adhered together by a conductive adhesive 27. The backing 28 is dimensioned and of such a material as to absorb ultrasonic waves from the backside of the transducer 22 so that only energy from the front side of the transducer is emitted from the imaging probe 14 in the general direction indicated by reference character 30 transverse to the exposed surface of the transducer 22. The coaxial cable 20 extends down the drive shaft 18 and includes a center conductor 32 and a shield lead 34. The center conductor 32 and shield lead 34 are coupled across the transducer 20 as shown. The coaxial cable 20 couples energy to the transducer to cause the transducer 22 to generate a pressure wave into the lumen 36 of the sheath 12. The interior of the lumen 36 is preferably filled with a fluid, such as saline. The saline flows from the proximal end of the catheter 10 to the distal end of the catheter 10 and serves to efficiently couple the ultrasonic energy into the sheath and then to the body. To support the fluid flow, the sheath includes a point of egress (not shown) for the fluid at its distal end. As previously mentioned, it is important to prevent air bubbles from being formed or residing in the vicinity of the transducer 22.

Figure 2:
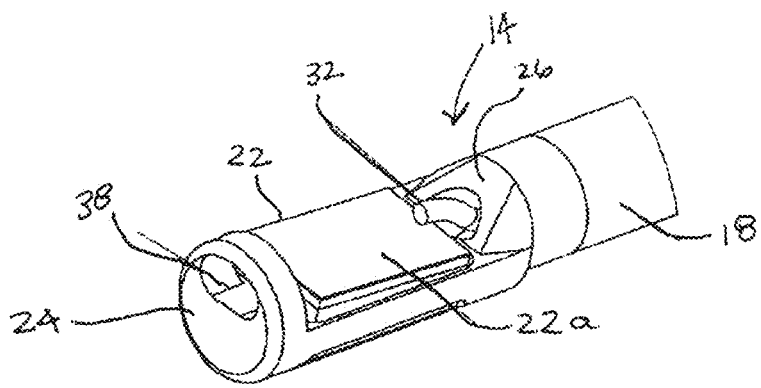
FIG. 2 is a partial perspective view of the imaging probe of the catheter of FIG. 1.

To assure that air bubble formation in the vicinity of the transducer 22 is prevented, and with additional reference to FIG. 2, the distal extent of the distal housing 16 includes a distal tip wall 24 distal and adjacent to the transducer 22. The distal tip wall 24 has an opening 38 therein adjacent to the transducer 22. Proximal to the transducer 22, the distal housing 16 has a proximal cutout forming a tapered surface 26 leading toward the transducer 22. Fluid flow within the sheath from proximal to the transducer 22 to distal of the transducer 22 is conducted down the tapered cutout surface 26, over the transducer 22, and out the distal tip wall opening 38 in a continuous manner, without turbulence, to prevent air bubble formation in the vicinity of the transducer.

The distal housing 16 at the proximal extent of the tapered cutout surface 26 has or defines a first profile substantially transverse to the catheter center axis 40 and the fluid flow. The distal tip wall 24 defines a second profile also substantially transverse to the catheter center axis 40 and the fluid flow. The second profile is greater in dimension than the first profile. Hence, this serves to promote fluid flow through the distal tip opening 38 and hence over the transducer 22.

To further promote fluid flow over the transducer 22, the transducer has a surface 22a over which the fluid flows that is disposed at an angle sloping toward the catheter center axis in the proximal direction. This presents a greater surface resistance against the fluid flow to assure fluid contact therewith.

FIG. 3 shows another imaging catheter 110 according to a further embodiment of the present invention. The catheter 110 is similar to the catheter 10 of FIGS. 1 and 2 and hence, reference characters for like elements are repeated in FIG. 3. To further assure that air bubble formation in the vicinity of the transducer 22 is prevented during rotational operation, and with additional reference to FIG. 3, the proximal extent of the distal housing 26 is constructed with aqua ducts 41 and 42. As shown in FIG. 3, one aqua duct directs fluid onto the transducer face 22 from the top of the proximal portion of the distal housing 26, while the other aqua duct 41 directs fluid onto the transducer face 22 from the side. Further, the aqua ducts are built into the proximal portion 26 of the distal housing 16 at an angle with respect to a line extending along the catheter drive shaft. This is shown in FIG. 3 with the angle theta being formed with the intersection of a line 43 extending parallel to the catheter drive shaft 13 and a line 44 extending through the center of one of the aqua ducts 41. Both aqua ducts 41 and 42 are constructed at such an angle such that the proximal side of each duct leads the distal side in the direction of rotation. This is shown in FIG. 3 with the clockwise direction of rotation (from the view looking distally along the catheter drive shaft 13) indicated by 45. Further, each side of each aqua duct is constructed with a small radius of curvature shown by 46 in FIG. 3. One way to achieve the duct side curvatures is to construct the ducts in a helical spiral with a small pitch, as, for example, on the order of 0.1 inch. The duct angle and curvature, coupled with rotation of the distal housing 16 and the fluid flow promoting structure shown in FIG. 1, act to continuously draw fluid from the catheter sheath 12 onto the face of the transducer 22. Fluid flow within the sheath from proximal to the transducer 22 to distal of the transducer 22 is conducted down the tapered cutout surface 26, over the transducer 22, and out the distal tip wall opening 38 in a continuous manner, without turbulence, to prevent air bubble formation in the vicinity of the transducer.

While particular embodiments of the present invention have been shown and described, modifications may be made, and it is therefore intended in the appended claims to cover all such changes and modifications which fall within the true spirit and scope of the invention as defined by those claims.

What is claimed is:

1. An imaging probe for use in a catheter for ultrasonic imaging, the imaging probe comprising:
   a transducer backing;
   a transducer disposed near a distal end of the imaging probe, the transducer configured to generate and receive ultrasonic waves, the transducer including a first surface and a second surface that is opposite the first surface, the first surface facing the transducer backing, and the second surface comprising a proximal edge and a distal edge, the proximal edge being axially closer to a proximal end of the imaging probe, the distal edge being axially closer to the distal end of the imaging probe;
   wherein the second surface is inclined with respect to a catheter center axis so that the proximal edge of the second surface is radially closer to the catheter center axis than the distal edge of the second surface, and
   wherein the imaging probe further comprises a distal tip wall disposed distal to the transducer, the distal tip wall including a distal tip wall opening, such that a direction of the inclined second surface and a position of the distal tip wall opening allow a fluid to flow distally along the catheter, to pass over the second surface of the transducer and to exit the catheter through the distal tip wall opening.

2. The imaging probe of claim 1, wherein the second surface is configured to facilitate non-turbulent fluid flow over the second surface to prevent air bubble formation at the transducer.

3. The imaging probe of claim 1, wherein the transducer backing includes a backing surface facing the first surface of the transducer, and wherein the backing surface is disposed at an angle sloping toward the catheter center axis in the proximal direction.

4. The imaging probe of claim 3, wherein the first surface is disposed at an angle sloping toward the catheter center axis in the proximal direction.

5. The imaging probe of claim 1, further comprising:
a drive shaft configured to move the transducer,
wherein the second surface includes a proximal end and a distal end that is opposite the proximal end, the proximal end being closer to the drive shaft than the distal end, and wherein the distal end is at a different elevation than the proximal end.

6. The imaging probe of claim 5, wherein the distal end is further from the catheter center axis than the proximal end.

7. The imaging probe of claim 5, further comprising:
a conductor coupled to the transducer at the proximal end.

8. The imaging probe of claim 1, further comprising:
a housing supporting the transducer backing and the transducer, the housing including fluid flow promotion means for promoting flow of fluid over the second surface of the transducer to prevent air bubble formation near the transducer.

9. The imaging probe of claim 8, wherein the fluid flow promotion means includes a tapered cutout surface at the housing proximal to the transducer.

10. The imaging probe of claim 8, wherein the fluid flow promotion means includes an aqua duct formed in an outer surface of the housing at an angle to the catheter center axis.

11. The imaging probe of claim 1 further comprising:
a housing supporting the transducer, the housing including an aqua duct formed in an outer surface of the housing at an angle to a catheter center axis, wherein the aqua duct is configured to direct fluid onto the transducer.

12. The imaging probe of claim 11, further comprising:
a drive shaft coupled to the housing and configured to rotate the housing in a direction of rotation,
wherein the aqua duct includes a proximal end and a distal end, and wherein the aqua duct is formed in the outer surface of the housing such that the proximal end of the aqua duct leads the distal end of the aqua duct in the direction of rotation.

13. The imaging probe of claim 11, further comprising:
a second aqua duct formed in the outer surface of the housing at an angle to the catheter center axis.

14. The imaging probe of claim 13, wherein the second aqua duct includes a proximal end and a distal end, and wherein the second aqua duct is formed in the outer surface of the housing such that the proximal end of the second aqua duct leads the distal end of the second aqua duct in the direction of rotation.

15. The imaging probe of claim 13, wherein the distal end of one of the aqua duct and the second aqua duct is positioned to direct fluid onto a face of the transducer from a top of the transducer and the distal end of the other of the aqua duct and the second aqua duct is positioned to direct fluid onto the face of the transducer from a side of the transducer.

16. The imaging probe of claim 13, further comprising a tapered cutout surface at the housing proximal to the transducer, wherein the tapered cutout surface is disposed at the housing between the aqua duct and the second aqua duct.

17. The imaging probe of claim 11, wherein the aqua duct is formed in the outer surface of the housing as a helical spiral.

18. The imaging probe of claim 17, where the aqua duct has a pitch of approximately 0.1 inch.

19. An imaging probe for use in a catheter for ultrasonic imaging, the imaging probe comprising:
a distal housing disposed near a distal end of the imaging probe;
a transducer backing disposed in the distal housing;
a transducer disposed in the distal housing, the transducer configured to generate and receive ultrasonic waves, the transducer including a first surface and a second surface that is opposite the first surface, the first surface facing the transducer backing, and the second surface disposed at an angle to a catheter center axis; and
a distal tip wall disposed distal to the transducer, the distal tip wall including a distal tip wall opening,
wherein the angle of the second surface of the transducer presents a greater surface resistance against a fluid flowing within the catheter towards the distal end of the imaging probe, and
wherein the distal tip wall opening is positioned to receive the fluid flowing within the catheter across the second surface of the transducer.

20. The imaging probe of claim 19 wherein the second surface comprises a proximal edge and a distal edge, the proximal edge disposed axially closer to a proximal end of the imaging probe, the distal edge disposed axially closer to the distal end of the imaging probe, and wherein the second surface of the transducer is angled with respect to a catheter center axis so that the proximal edge of the second surface is radially closer to the catheter center axis than the distal edge of the second surface.

* * * * *